United States Patent [19]

Yan

[11] Patent Number: 5,053,209
[45] Date of Patent: Oct. 1, 1991

[54] REMOVAL OF MERCURY FROM NATURAL GAS AND LIQUID HYDROCARBONS UTILIZING SILVER ON ALUMINA ADSORBENT

[75] Inventor: Tsoung Y. Yan, Philadelphia, Pa.

[73] Assignee: Mobil Oil Corporation, Fairfax, Va.

[21] Appl. No.: 332,149

[22] Filed: Apr. 3, 1989

Related U.S. Application Data

[60] Division of Ser. No. 145,016, Jan. 9, 1988, abandoned, which is a continuation-in-part of Ser. No. 911,185, Sep. 24, 1986, abandoned.

[51] Int. Cl.$^5$ .............................................. B01D 47/00
[52] U.S. Cl. ..................................... 423/210; 208/253
[58] Field of Search .................. 208/353, 292, 251 R, 208/296, 299, 253; 62/17, 18; 423/210; 585/820; 55/72, 75

[56] References Cited

U.S. PATENT DOCUMENTS 4,150,962  4/1979  Colton ...................................... 62/17

FOREIGN PATENT DOCUMENTS 2310795  12/1976  France .

Primary Examiner—Curtis R. Davis
Attorney, Agent, or Firm—Alexander J. McKillop; Charles J. Speciale

[57] ABSTRACT

Hydrocarbon liquids and gas, particularly gas to be processed in LNG plants, is treated to remove mercury by contacting it with free silver preferably on an activated carbon or gamma alumina support. The mercury amalgamates onto the metal. The gas can previously have been treated by contact with free sulfur to remove mercury.

22 Claims, 2 Drawing Sheets

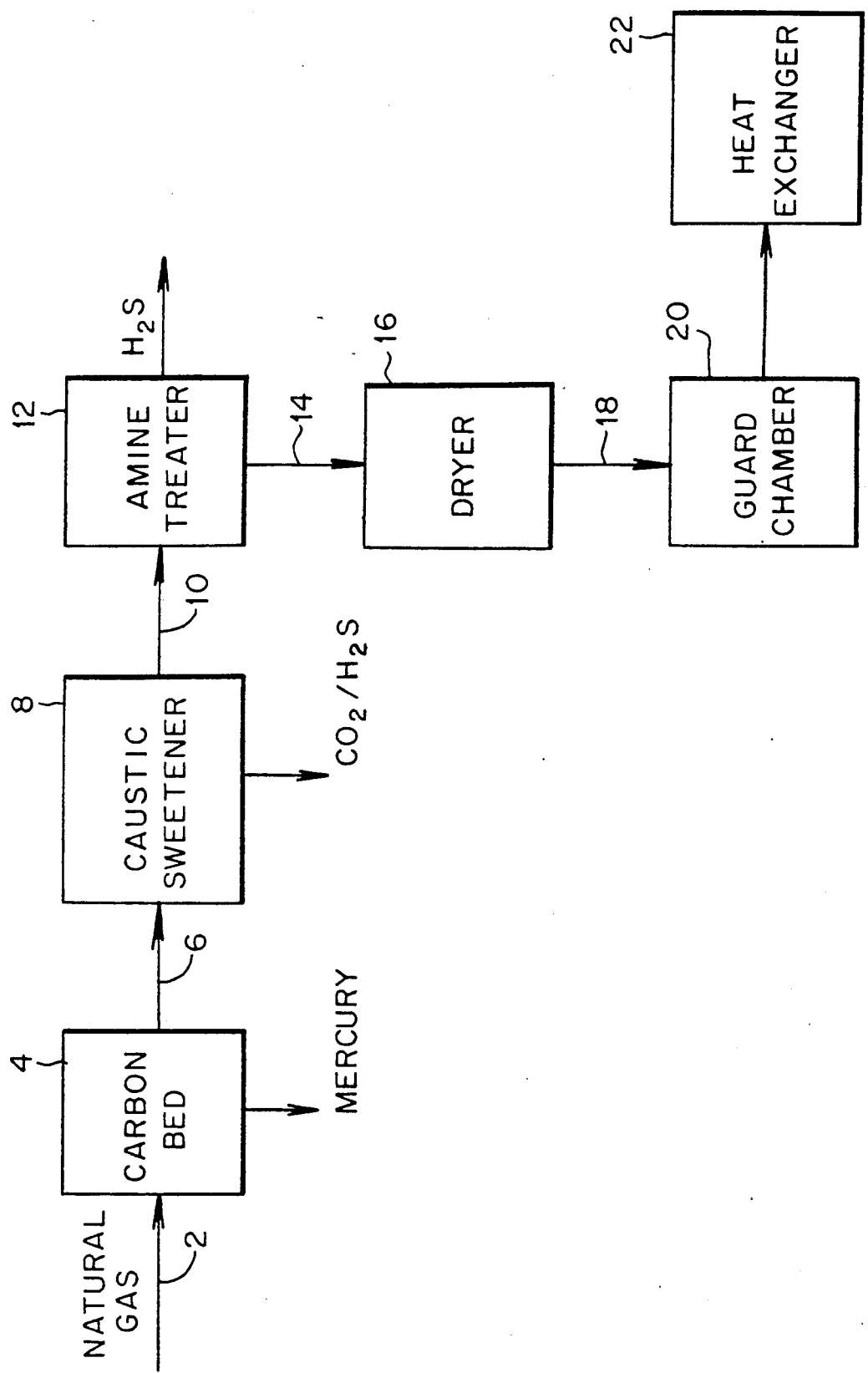

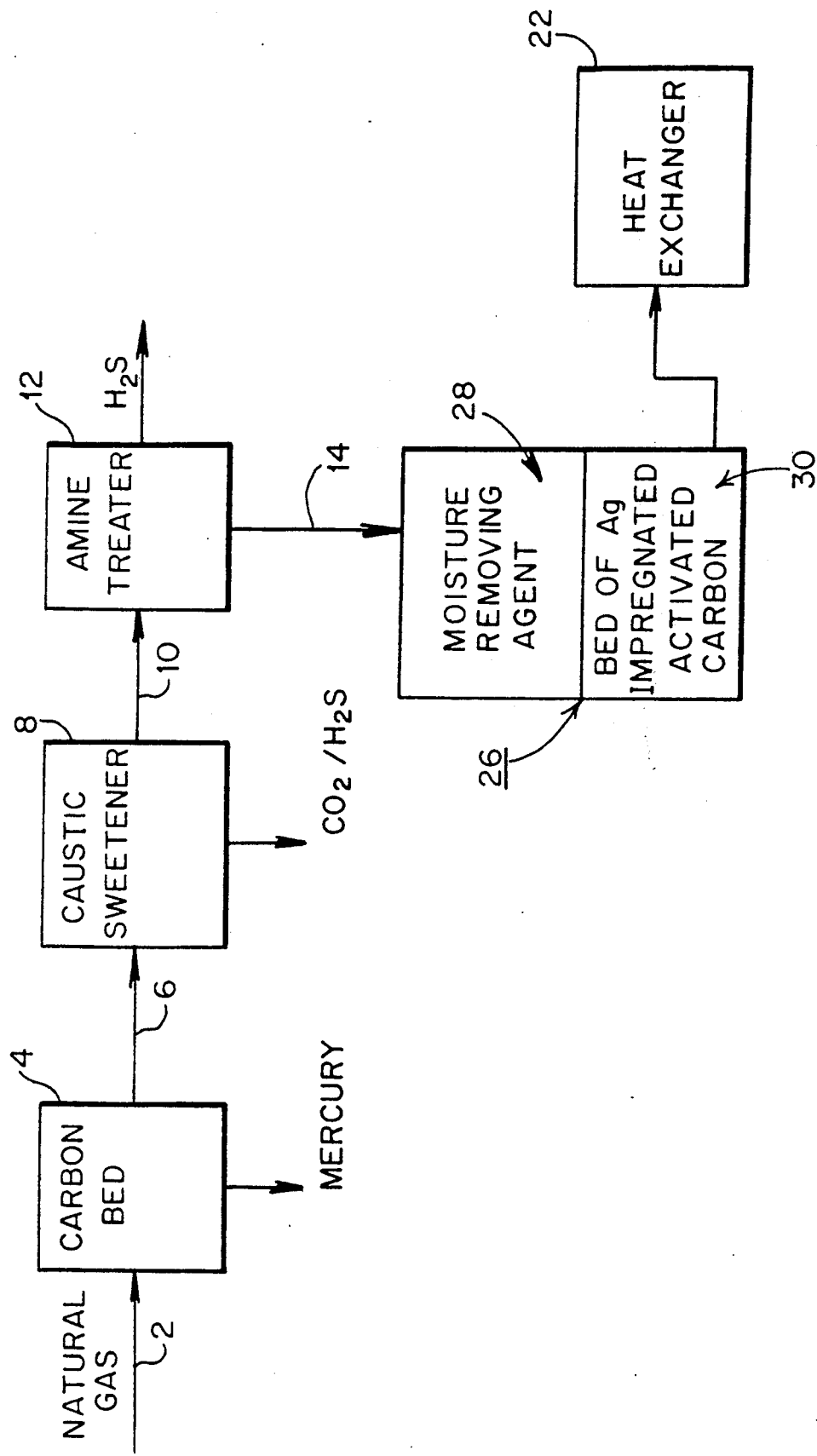

REMOVAL OF MERCURY FROM NATURAL GAS AND LIQUID HYDROCARBONS UTILIZING SILVER ON ALUMINA ADSORBENT

RELATED APPLICATIONS

This is a divisional of copending application Ser. No. 145,016, filed on Jan. 19, 1988 and now abandoned, which is a continuation-in-part of application Ser. No. 911,185, filed Sept. 24, 1986 and now abandoned.

NATURE OF THE INVENTION

This invention relates to a method for purifying and removing trace amounts of mercury and mercury compounds from natural gas.

PRIOR ART

Natural gas must be treated prior to its liquefaction for several reasons. These include removing compounds which interfere with the liquefaction process, with the separation and recovery of hydrocarbon liquids and with meeting the specifications set for the recovered products. For example, the gas must be dried to prevent ice formation during cryogenic operations. Hydrogen sulfide ordinarily must be removed because of its toxic nature. A large number of commercial processes are in use for treating and separating of raw wellhead gas. The steps used in these different processes are each well known to those skilled in the art.

Natural gas contains mercury at levels as high as 200 to 300 micrograms per cubic meter. For example, the mercury level of natural gas produced from one field is reported in the literature to range from 200 to 330 micrograms per cubic meter. In another field the concentration was reported to range between 15 and 450 micrograms per cubic meter. The processing of natural gas in LNG plants ordinarily requires contact with equipment made primarily of aluminum. The crude gas is treated by caustic or carbonate washing to remove $CO_2$ and $H_2S$ and then to treatment with liquid amine to complete $H_2S$ removal. One of the next steps is to chill or cool the gas in aluminum-constructed heat exchangers. Because large volumes of gas must be flowed through the aluminum heat exchangers they are of a massive size and can represent a capital investment of several million dollars. Damage to these exchangers is to be avoided, if at all possible. One threat of damage comes from the mercury present in the gas flowing through the heat exchangers. Although the concentration of mercury appears low, its effect is cumulative as it reacts by amalgamation with the aluminum. The result is damage to the system, such as corrosion cracking, which can lead to equipment failure, fires, and similar catastrophes. Repair is correspondingly difficult because of damage to the welds of the aluminum. Replacement of the heat exchangers represents a large expenditure. The down-time results in loss of production. The problem of mercury in natrual gas is discussed further in U.S. Pat. No. 4,094,777 and French Patent 2,310,795, both of which are incorporated herein by reference.

Accordingly, one object of this invention is to remove the mercury present in natural gas to a concentration sufficiently low to protect liquefaction equipment, such as the aluminum heat exchangers, in a liquefied natural gas plant. Another object is to minimize the release of mercury vapors into the environment. Still another objective is to provide a process for mercury removal which can be integrated into current gas and liquid purification systems at existing LNG plants.

DESCRIPTION OF THE DRAWING

FIG. 1 is a flow sheet presenting one embodiment of the invention described herein.

FIG. 2 is a modified flowsheet of FIG. 1 showing a second and preferred modified embodiement of the invention.

SUMMARY OF THE INVENTION

In a broad sense this invention comprises a process for treating raw natural gas prior to liquefaction which comprises (a) passing a stream of raw natural hydrocarbon gas or liquid through a zone containing activated carbon impregnated with sulfur, at conditions effective to remove mercury from said natural gas; (b) passing the effluent stream of natural gas thus treated through a sweetening zone operating at conditions effective to remove carbon dioxide and hydrogen sulfide and/or then passing the effluent stream through an amine treating system where additional hydrogen sulfide is removed, (c) subsequently passing the effluent through a drier or dehydrator where water vapor is removed and (d) finally passing the effluent through a heat exchanger to a further product treatment zone. In this invention there is positioned in the flow line, preferably downstream of the dehydrator, or dryer, a body of activated carbon, silica, alumina, or silica-alumina supports, which can be honeycomb shaped, extrudate, granules, beads, and pellets containing free silver in an active state such that it forms an amalgam with mercury. The silver preferably is deposited in a dispersed form on activated carbon, or even more preferably on gamma alumina, although other supports can be used such as silica, other aluminas such as alpha or beta, and silica-alumina. This technique is particularly useful in removing the residual mercury still remaining in the gas stream even after it has been treated under optimum operating conditions by equipment located upstream.

DETAILED DESCRIPTION OF THE INVENTION

In the prior art the most popular absorbent used to remove mercury is sulfur loaded on activated carbon. The reaction between the sulfur and mercury is:

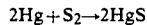

$$2Hg + S_2 \rightarrow 2HgS$$

It is important to recognize that this reaction is a reversible one. This reaction can be carried out efficiently but the extent of mercury removal is limited by the thermodynamic equilibrium. For instance, at 170° F., thermodynamic equilibrium dictates that the residual Hg in the gas stream cannot be lower than 0.03 ppb. Commercial experience has shown this level of Hg in the natural gas to be too high for critical equipment in LNG plants to tolerate when large volumes are processed. Thus, the further removal of this residual mercury is necessary. Because thermodynamic properties limit the amount of mercury removed, the removal unit cannot be made efficient by mechanical improvement. Although lowering the reaction temperature will improve the thermodynamic limitation, the reaction rate is lowered and the life of the absorbent is shortened correspondingly. The optimum operating temperature has been determined to be about 170° F.

This invention accordingly in part comprises removing mercury from natural gas utilizing substrates other than sulfur to react with, collect, and still further reduce mercury concentrations.

The substrate utilized in the method of this invention is metallic silver dispersed preferably on activated carbon or on gamma alumina. Other usable support materials include other types of alumina, silica, silica-alumina, silicates, aluminates and silica aluminates, as well as synthetic and natural zeolites, to increase the metal surface area to greater than $0.01 m_2/g$ to improve activity for mercury removal. The concentration of silver metal on the activated carbon or gamma alumina should be between 0.1 and 20 percent by weight (preferably between 1 and 5 percent). The silver can be dispersed onto the carrier by impregnation, coprecipitation or other well known methods. The absorbent can be in the form of extrudate, beads, pellets and granules. Pressure drop across a body of absorbent can be minimized by using absorbent in the form of honeycomb, or "multi-lobe" configuration.

Referring now to the accompanying drawings, and in particular to FIG. 1, natural gas feed is introduced through line 2 into carbon bed 4 which contains free sulfur deposited on granulated carbon. The bed functions to fix or adsorb a large fraction of the mercury vapor present in the natural gas by interaction with the sulfur. The effluent gas therefrom is then introduced from line 6 into a zone 8 containing preferably a hot aqueous solution of an alkali carbonate, preferably potassium carbonate, at a temperature of about 200° to about 300° F. These hot carbonate processes for sweetening natural gas are known in the art. Most of them contain a proprietary activator, for example the Benfield process, the Catacarb process and the Giammarco-Vetrocoke process. These processes are discussed in U.S. Pat. Nos. 4,150,962 and 4,070,165, both of which are incorporated herein by reference. The effluent gas from the hot carbonate process is carried through conduit 10 to an amine treating unit 12 for additional processing and removal of hydrogen sulfide. The effluent from the amine treater 12 is flowed by means of conduit 14 through a dehydrator (dryer) 16 where water vapor is removed from the gas and subsequently into a guard chamber 20 which is filled with reactive silver metal dispersed preferably on activated carbon. The support for the free metal or metals preferably is of a honeycomb or multi-lobe configuration. Honeycomb and multi-lobe forms are available commercially. The silver component on the absorbent removes mercury from the gas stream by reacting with the mercury to form amalgam. The absorbent must be reactive with the mercury so that a high throughput of gas or liquid can be achieved.

Referring again to FIG. 1, the effluent gas from the guard chamber 20 is then passed through a heat exchanger 22 and to other additional equipment needed for further processing of the gas. The heat exchanger 22 ordinarily will be made of aluminum and is the particular component of the process from which this invention is intended to protect from attack by mercury. As noted previously, this particular component, because of its aluminum construction, is particularly vulnerable. It's cost of installation, as well as replacement value in many cases where large volumes of gas are processed, can be a substantial capital expenditure.

A preferred method of practicing this invention is presented in FIG. 2 where like-numbered functions are the same as those in the description of the process of FIG. 1. In this method the moisture-removing agent is present in the upstream section 28 of the dryer 26 and a bed 30 of the silver-impregnated activated carbon is positioned in the lower part of the dryer bed. The gas is thus first dried and then depleted of mercury by the supported silver catalyst. It is also possible to fill the dryer zone completely or the lower half section of the drier with a mixture of drying agent and mercury adsorption agent. Mixing the drying agent and the mercury adsorption agent provides the advantage of not adding a new piece of equipment to an existing installation and introducing additional pressure drops into the system. The mercury adsorbent must however be regenerable at the regeneration conditions for the drier or present in sufficient quantity that it need not be replaced until the drier absorbent material is replaced. The volume of mercury adsorbent placed in the drying zone should be between 1 and 20 percent by volume, preferably between 2 and 10 percent of the total volume.

EXAMPLE

An adsorbent consisting of silver deposited on gamma alumina was prepared by saturating the gamma alumina with an aqueous solution of silver nitrate, drying and calcining the impregnated alumina, and then reducing the silver nitrate to free metallic silver by contacting the alumina with formaldehyde. The adsorbent contained approximately 5 percent by weight of silver. An initial test of the adsorbent in which 0.1 gram of the adsorbent was contacted with 100 milliliters of air equilibrated with mercury indicated that 98 percent of the mercury in the air was removed.

One-tenth (0.1) gram of the fresh adsorbent was contacted with 1442 liters of nitrogen containing about 1.5 ppb mercury at a flow rate of 250 cc at room temperature. The treated gas was determined to contain 0.012 ppb of mercury, equivalent to a removal efficiency of 99 percent.

Other tests have shown that a nitrogen stream containing 0.25 ppb of mercury could be treated with the same type of silver-on-alumina catalyst to provide a treated gas containing in one test 0.068 ppb mercury and in another experiment 0.0062 ppb mercury.

The adsorbent loaded with mercury was regenerated successfully with hot gases at 350°–450° C. Upon regeneration the adsorbent had become effective for mercury adsorption again. The mercury adsorbent thus can be employed in the drier under conditions where it is mixed directly with the water-sorbent material.

Although the emphasis of this disclosure has been on gas processing such as in a LNG plant, this invention has utility where hydrocarbon liquids containing undesired concentrations of mercury are present. It will be understood by those skilled in the art that in processing liquids, problems associated with freeze ups and the like may be encountered and must be compensated for.

What is claimed is:

1. In a process wherein a hydrocarbon gas or liquid containing an undesired level of water and mercury is passed through a flow system comprising a drying zone comprising a drying agent upstream of aluminum equipment, the improvement comprising inserting into the drying zone a free silver reactant capable of forming an amalgam with said mercury and of being regenerated at the regeneration conditions for the drying agent.

2. The process of claim 1 wherein the free silver reactant is supported on a support selected from the group consisting of carbon, alumina, silica, silica-alumina, silicates, aluminates, and silica aluminates and mixtures thereof.

3. The process of claim 1 wherein the free silver reactant is supported on a support having the form of extrudates, granules, beads or pellets in a honey-comb shape or multilobe configuration.

4. The process of claim 1 wherein the free silver reactant is supported on an activated carbon support.

5. The process of claim 1 wherein the free silver reactant is supported on a gamma alumina support.

6. The process of claim 1 wherein the volume of mercury adsorbent in the drying zone is between 1 and 20%.

7. The process of claim 1 wherein the volume of mercury adsorbent placed in the drying zone is between 2 and 10%.

8. A process for the treatment of raw natural hydrocarbon gas containing water and mercury prior to liquefaction, which comprises:
   (a) passing said stream of raw natural gas through an aqueous sweetening zone under conditions effective to remove carbon dioxide and hydrogen sulfide, thereby forming a stream of sweetened natural gas containing mercury;
   (b) passing the resulting stream of sweetened natural gas through adsorbent agent containing free silver dispersed on a support, the drying zone containing a drying agent operated at condition effective to remove water and mercury therefrom and to effect the formation of a stream of a dried natural gas substantially free of mercury;
   (c) recovering the resultant stream having a substantially decreased mercury content; and
   (d) simultaneously regenerating the drying agent and mercury adsorption agent.

9. The process of claim 8 wherein step (a) includes contacting said natural gas stream with free sulfur deposited on a support.

10. The process of claim 8 wherein the free silver is dispersed on a non-reactive carbon support.

11. The process of claim 8 wherein the free silver is dispersed on an activated carbon support.

12. The process of claim 8 wherein the free silver is dispersed on a gamma alumina support.

13. The process of claim 8 further characterized in that the sweetening zone comprises an aqueous alkaline solution.

14. The process of claim 8 wherein the mercury adsorbent is positioned in the bottom of the drying zone.

15. The process of claim 8 wherein the mercury adsorbent is mixed with drying agent and contained within the lower section of the drying zone.

16. The process of claim 8 wherein the mercury adsorbent is mixed with drying agent throughout the whole drying zone.

17. The process of claim 8 wherein the sweetening zone is an amine treater.

18. In a process for eliminating water and mercury present in a gas comprising contacting the gas with an absorption mass in a fixed bed, the improvement wherein the absorption mass is present in the drying zone, and consists essentially of:
   (a) a solid support selected from the group consisting of activated carbon, silica, alumina, silica-alumina, silicates, aluminates and silica aluminates; and
   (b) between about 0.5 and about 20% of silver in the reduced free metal state.

19. The process of claim 18 wherein the support is activated carbon.

20. The process of claim 18 wherein the support is gamma alumina.

21. The process of claim 8 wherein the raw natural gas is flowed through a preliminary apparatus for removing mercury from said gas prior to contacting the gas with the absorption mass.

22. The process of claim 21 wherein said preliminary apparatus contains an absorbent comprising sulfur on activated carbon.

* * * * *